(12) United States Patent
Yoda et al.

(10) Patent No.: US 10,918,261 B2
(45) Date of Patent: Feb. 16, 2021

(54) POWER SUPPLY CONTROL SYSTEM AND POWER SUPPLY CONTROL METHOD

(71) Applicant: OLYMPUS CORPORATION, Hachioji (JP)

(72) Inventors: Hisashi Yoda, Tokyo (JP); Hiroyuki Ushifusa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 9 days.

(21) Appl. No.: 16/359,054

(22) Filed: Mar. 20, 2019

(65) Prior Publication Data

US 2019/0216293 A1    Jul. 18, 2019

Related U.S. Application Data

(63) Continuation of application No. PCT/JP2017/038120, filed on Oct. 23, 2017.

(30) Foreign Application Priority Data

Dec. 21, 2016  (JP) .............................. JP2016-247797

(51) Int. Cl.
*B60R 16/02*  (2006.01)
*G06F 1/26*  (2006.01)
(Continued)

(52) U.S. Cl.
CPC ...... *A61B 1/00027* (2013.01); *A61B 1/00006* (2013.01); *G06F 1/26* (2013.01); *G06F 1/30* (2013.01); *G05B 2219/25387* (2013.01)

(58) Field of Classification Search
USPC .......................................................... 307/31
See application file for complete search history.

(56) References Cited

U.S. PATENT DOCUMENTS

| 5,815,409 A | 9/1998 | Lee et al. |
| 2005/0192723 A1* | 9/2005 | Noguchi ................ G07C 5/085 |
| | | 701/33.4 |

FOREIGN PATENT DOCUMENTS

| JP | H09-198168 A | 7/1997 |
| JP | 2001-030579 A | 2/2001 |

(Continued)

OTHER PUBLICATIONS

Dec. 12, 2017 International Search Report issued in International Patent Application No. PCT/JP2017/038120.

(Continued)

*Primary Examiner* — Rexford N Barnie
*Assistant Examiner* — Xuan Ly
(74) *Attorney, Agent, or Firm* — Oliff PLC

(57) ABSTRACT

A power supply control system includes a power supply circuit that supplies power, an electronic component that is operable by the power supplied from the power supply circuit, starts shutdown processing in response to an input of a stop instruction signal, and operates when an operation instruction signal is input, and a signal control circuit that receives a power input state signal or a power cutoff state signal as a power state signal indicating a state of the power supply circuit, outputs the stop instruction signal when the power cutoff state signal is input, outputs the operation instruction signal when the power input state signal is input, and outputs the stop instruction signal at least during the shutdown processing when the power input state signal is input in a case in which the shutdown processing of the electronic component is not finished.

6 Claims, 10 Drawing Sheets

(51) Int. Cl.
*A61B 1/00* (2006.01)
*G06F 1/30* (2006.01)

(56) References Cited

FOREIGN PATENT DOCUMENTS

| | | |
|---|---|---|
| JP | 2001-331240 A | 11/2001 |
| JP | 2001331240 | * 11/2001 |
| JP | 2003-032885 A | 1/2003 |
| JP | 2005-240771 A | 9/2005 |

OTHER PUBLICATIONS

Dec. 12, 2017 Written Opinion issued in International Patent Application No. PCT/JP2017/038120.
Dec. 11, 2018 Office Action issued in Japanese Patent Application No. 2018-557577.

* cited by examiner

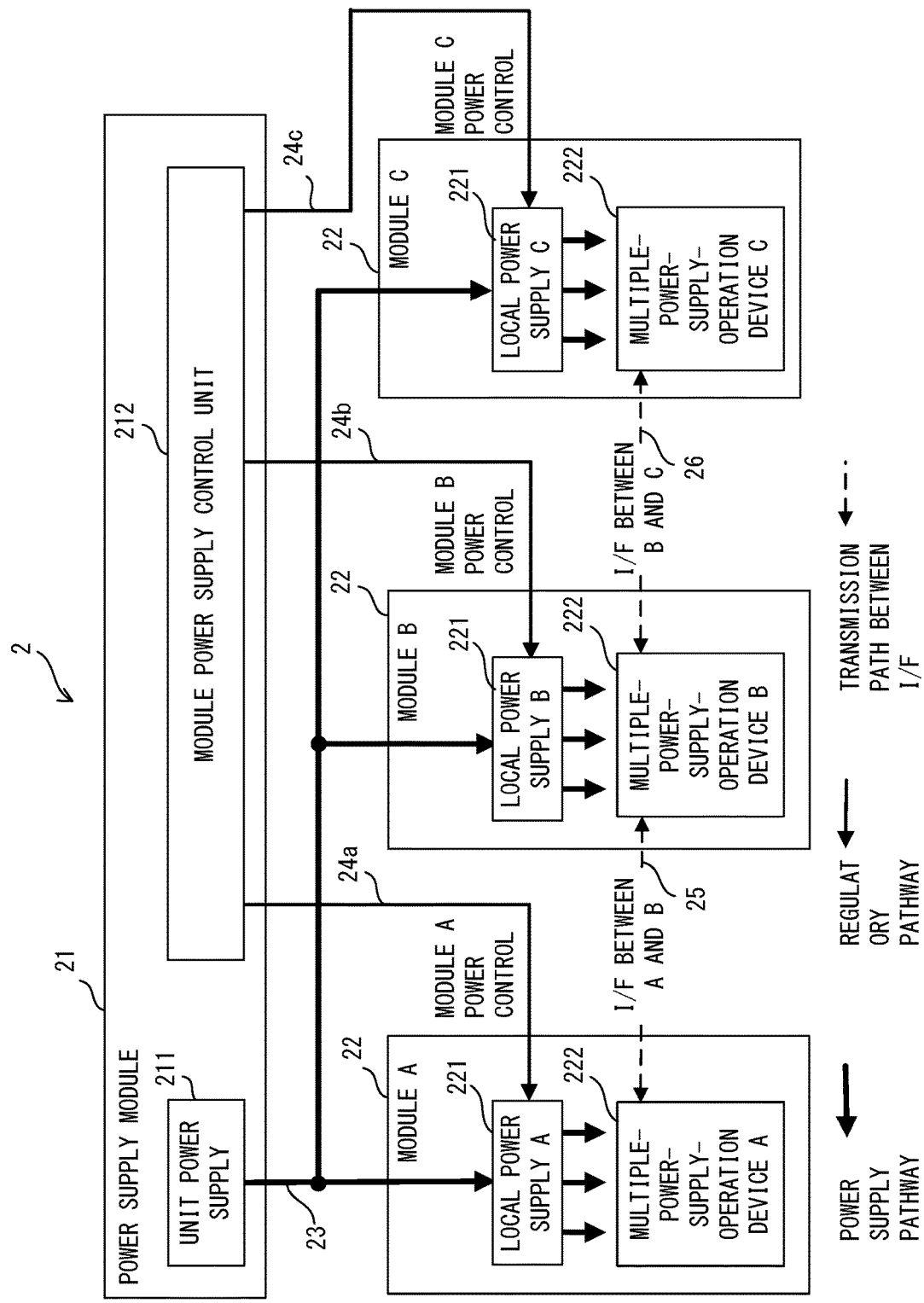
F I G. 4

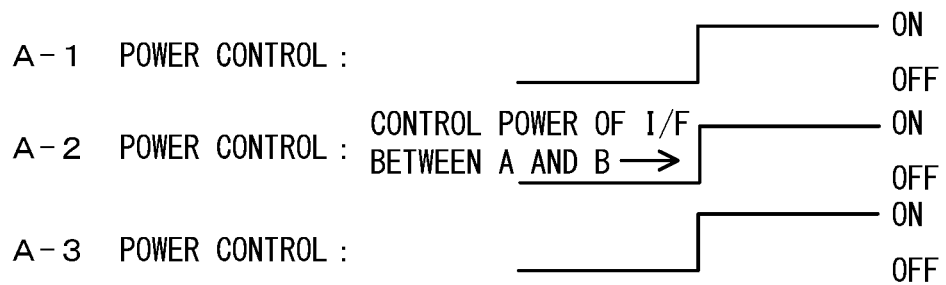
F I G. 5

POWER SUPPLY CONTROL SYSTEM AND POWER SUPPLY CONTROL METHOD

CROSS-REFERENCE TO RELATED APPLICATIONS

This application is based upon and claims the benefit of priority of the prior Japanese Patent Application No. 2016-247797, filed Dec. 21, 2016, the entire contents of which are incorporated herein by reference.

This is a Continuation Application of PCT Application No. PCT/JP2017/038120, filed Oct. 23, 2017, which was not published under PCT Article 21(2) in English.

FIELD

The present invention relates to a power supply control system and a power supply control method to perform power supply control of electronic components.

BACKGROUND

Endoscope processors have been heretofore used in endoscopic examinations performed in medical institutions such as hospitals. An endoscope processor is a device that processes video signals captured by an endoscope (scope) inserted into the body cavity of a patient, records or displays the video signals, and performs other operations. An endoscope processor is also called an endoscope video processor or an endoscope video signal processor.

An endoscope processor is provided with electronic components (e.g., an endoscope driver circuit), a power supply unit to supply power to the electronic components, and others. A power supply unit has an AC (Alternating Current)-DC (Direct Current) converter circuit (may also be called an AC-DC converter) and converts the primary power (AC) input into the secondary power (DC) by the AC-DC converter circuit to supply (output) to the electronic components.

In the above-described endoscope processor, when a power supply switch is turned off and the primary power input is cut off, for example, the power supply unit uses electrical charge charged in a capacitor in the AC-DC converter circuit so that the output of the secondary power is maintained for a prescribed period of time. At that time, in the electronic components, shutdown processing that includes initializing of the internal settings is carried out during the prescribed period of time, afterwards the electronic components becomes a state of ready for cutoff of the secondary power, and the operations are stopped in a normal way.

There are other examples of the device in which even when a power supply switch is turned off, power supply is maintained until shutdown processing (or similar processing) is finished. For example, a control device for automatic cutoff of a power supply has been known in which, when a power switch is turned off, a power-supply state is maintained until prescribed cutoff processing is completed (see Japanese Laid-open Patent Publication No. H09-198168). For another example, a printer device has been known that is provided with a power supply switch and a power supply controller that directly turns off the power supply after a prescribed period of time in response to reception of an OFF signal from the power supply switch, and prescribed terminating processing is executed within the prescribed period of time from the power supply switch is turned off (i.e., before the power supply is actually cut off) (see Japanese Laid-open Patent Publication No. 200130579).

SUMMARY

One aspect of the present invention includes a power supply control system including a power supply circuit that supplies power, an electronic component that is electrically coupled to the power supply circuit, that is operable by the power supplied from the power supply circuit, that starts shutdown processing in response to an input of a stop instruction signal, and that operates when an operation instruction signal is input, and a signal control circuit that is electrically coupled to the electronic component, that receives a power input state signal or a power cutoff state signal as a power state signal indicating a state of the power supply circuit, that outputs the stop instruction signal when the power cutoff state signal is input, that outputs the operation instruction signal when the power input state signal is input, and that outputs the stop instruction signal at least during the shutdown processing when the power input state signal is input in a case in which the shutdown processing of the electronic component is not finished.

Another aspect of the present invention is a power supply control method that receives an input of a power input state signal or a power cutoff state signal as a power state signal indicating a state of a power supply circuit that supplies power to an electronic component, outputs a stop instruction signal to the electronic component when the power cutoff state signal is input and causes the electronic component to start shutdown processing, and outputs the stop instruction signal to the electronic component at least during the shutdown processing when the power input state signal in input in a case in which the shutdown processing of the electronic component is not finished.

BRIEF DESCRIPTION OF DRAWINGS

FIG. 4 is a diagram illustrating an example of configuration of an endoscope processor that is the power supply control system according to the second embodiment.

FIG. 5 is a timing chart illustrating an example of a startup sequence of the multiple-power-supply-operation device A under the control of the local power supply A in module A.

DESCRIPTION OF EMBODIMENTS

In recent years, as the functions of endoscope processors become diversified, the number of electronic components provided in the endoscope processors tends to increase. As the number of electronic components increases, there are growing concerns about the following issues caused by differences in start timing of shutdown processing and in duration of the shutdown processing between the electronic components.

For example, a case is considered in which, due to an incorrect operation of a user etc., a power supply switch is turned on immediately after the power supply switch is turned off. At that time, the power supply switch is turned on before the elapse of the above-described prescribed period of time (a period of time in which the second power output is maintained by a capacitor) from a point in time at which the power supply switch is turned off. This case may result in a situation in which, for example, some electronic components restart before the shutdown processing, other electronic components restart during the shutdown processing, and the remaining electronic components restart after the shutdown processing. In other words, in this case, electronic components being restarted while leaving some or all of the internal setting uninitialized (i.e., some or all of the previous internal setting is maintained) and electronic components being restarted after the initialization of internal setting are present in one endoscope processor. As a result, differences are made in startup states (internal setting states) between the electronic components after restarting, and the endoscope processor may not normally operate after the restarting.

In view of the above circumstances, the embodiments disclosed below provide a power supply control system and a power supply control method that can eliminate the differences in the startup state between electronic components after restarting even when a power supply switch is turned on immediately after the power supply switch is turned off.

An explanation of embodiments is provided with reference to the drawings.

First Embodiment

Figure 1:
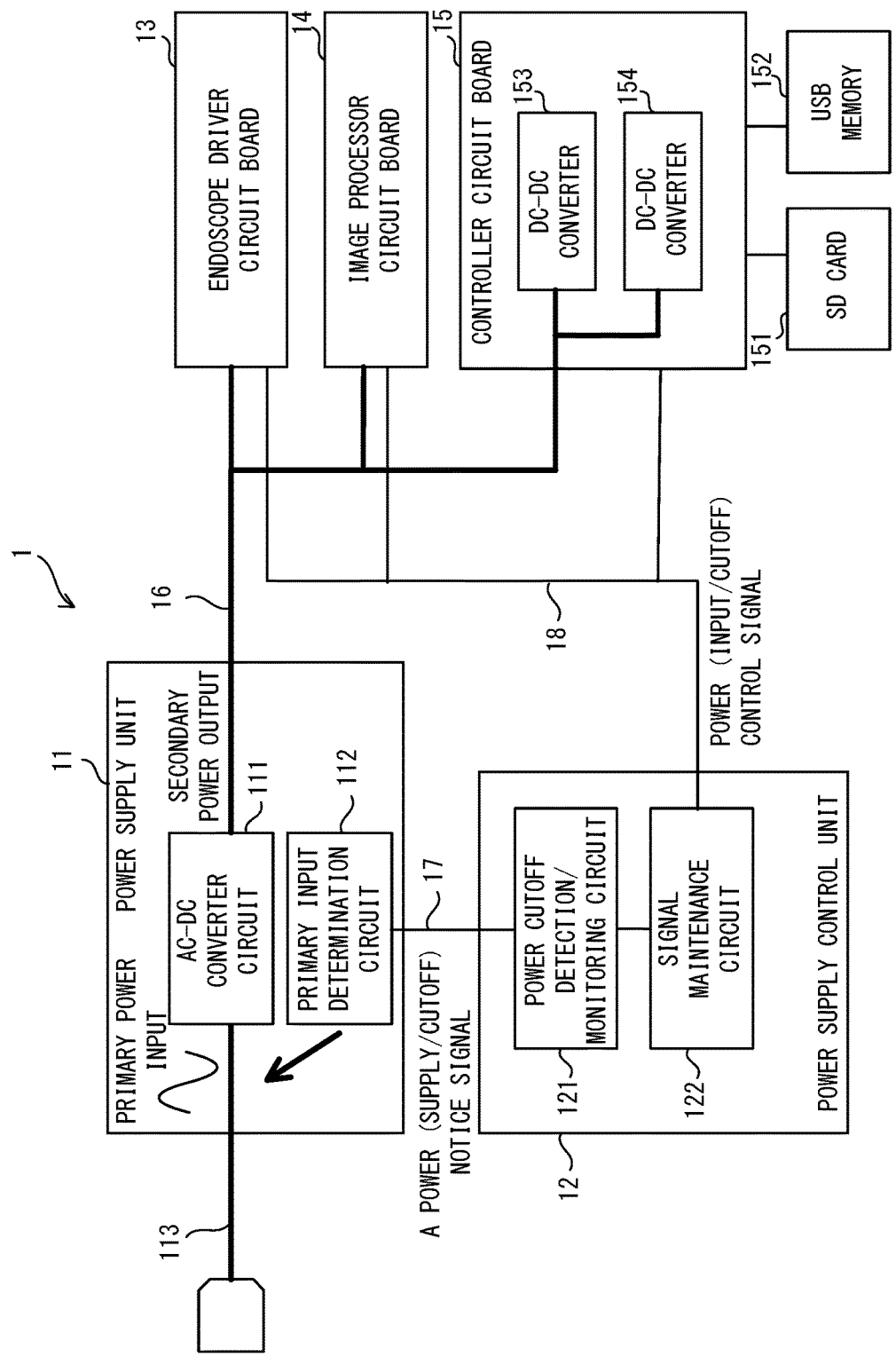
FIG. 1 is a diagram illustrating an example of configuration of an endoscope processor that is a power supply control system according to the first embodiment.

FIG. 1 is a diagram illustrating an example of configuration of an endoscope processor that is a power supply control system according to the first embodiment.

In FIG. 1, an endoscope processor 1 according to the first embodiment is used in endoscopic examinations performed in medical institutions such as hospitals and is a device that processes video signals captured by an endoscope inserted into the body cavity of a patient, records or displays the video signals, and performs other operations.

The endoscope processor 1 includes a power supply unit 11, a power supply control unit 12, an endoscope driver circuit board (endoscope driver circuit) 13, an image processor circuit board (image processor circuit) 14, and a controller circuit board (controller circuit) 15. The power supply unit 11, the endoscope driver circuit board 13, the image processor circuit board 14, and the controller circuit board 15 are electrically coupled to each other via a power supply line 16. The power supply unit 11 and the power supply control unit 12 are electrically coupled to each other via a signal line 17. The power supply control unit 12, the endoscope driver circuit board 13, the image processor circuit board 14, and the controller circuit board 15 are electrically coupled to each other via a signal line 18.

The power supply unit 11 supplies electrical power to the endoscope driver circuit board 13, the image processor circuit board 14, and the controller circuit board 15 via the power supply line 16. The power supply unit 11 includes an AC-DC converter circuit 111 and a primary input determination circuit 112.

The AC-DC converter circuit 111 converts the primary power (AC), which is externally input via a power supply cable 113, into the secondary power (DC) and outputs the secondary power to the endoscope driver circuit board 13, the image processor circuit board 14, and the controller circuit board 15 via the power supply line 16. The AC-DC converter circuit 111 also includes a capacitor that is not illustrated in the drawings and is configured to be able to maintain the secondary power output for a prescribe period of time A, which is described later, by using the charge in the capacitor, even when the primary power input is cut off.

The primary input determination circuit 112 determines whether the primary power, which is input via the power supply cable 113, is in an input state or is in a cutoff state and outputs a power notice signal (power supply notice signal or power cutoff notice signal) in accordance with the determination result to the power supply control unit 12 via the signal line 17. Note that in the present embodiment, the primary power is input to the power supply unit 11 when the power supply switch, which is not illustrated in the drawings, of the endoscope processor 1 (e.g., a push-button switch) is turned on, and the primary power input to the power supply unit 11 is cut off when the power supply switch is turned off. Accordingly, the primary input determination circuit 112 determines the primary power to be in an input state when the power supply switch is on and to be in a cutoff state when the power supply switch is off. The primary input determination circuit 112 outputs the power supply notice signal when determining the primary power to be in an input state and outputs the power cutoff notice signal when determining the primary power to be in a cutoff state.

The power supply control unit 12 controls the power supply to the endoscope driver circuit board 13, the image processor circuit board 14, and the controller circuit board 15 in response to the power notice signal input from the power supply unit 11 via the signal line 17. The power supply control unit 12 includes a power cutoff detection/monitoring circuit 121 and a signal maintenance circuit 122.

The power cutoff detection/monitoring circuit 121 controls outputs of the signal maintenance circuit 122 in response to the power notice signal input from the primary input determination circuit 122 via the signal line 17.

More specifically, the power cutoff detection/monitoring circuit 121 controls the output of the signal maintenance circuit 122 in such a manner that when the power notice signal input is switched from the power supply notice signal to the power cutoff notice signal, power cutoff control signal output is maintained as the output of the signal maintenance circuit 122 until the elapse of the prescribed period of time A from the point in time at which the power notice signal was switched.

In times other than the prescribed period of time A, the power cutoff detection/monitoring circuit 121 also controls the output of the signal maintenance circuit 122 as below. When the power notice signal input is a power supply notice signal, the power cutoff detection/monitoring circuit 121 controls the signal maintenance circuit 122 to output a power input control signal as an output. When the power notice signal input is a power cutoff notice signal, the power cutoff detection/monitoring circuit 121 controls the signal maintenance circuit 122 to output a power cutoff control signal as an output.

Note that the prescribed period of time A is a period of time needed from a point in time at which a power control signal (the power input control signal or the power cutoff control signal) input to the endoscope driver circuit board 13, the image processor circuit board 14, and the controller circuit board 15 is switched from the power input control signal to the power cutoff control signal to a point in time at which shutdown processing of each of the circuit boards is all finished.

Under the control of the power cutoff detection/monitoring circuit 121, the signal maintenance circuit 122 outputs a power control signal to the endoscope driver circuit board 13 the image processor circuit board 14, and the controller circuit board 15 via the signal line 18.

The endoscope driver circuit board 13 drives an endoscope, which is not illustrated in the drawings, coupled to the endoscope processor 1.

The image processor circuit board 14 performs prescribed image processing (e.g., image processing for recording) of video signals captured by the endoscope.

The controller circuit board 15 drives an SD card (an SD memory card) 151 and a USB (Universal Serial Bus) memory 152 coupled to the controller circuit board 15. The controller circuit board 15 includes DC-DC converters (also called DC-DC converter circuits) 153 and 154. Each of the DC-DC converters 153, 154 is a local power supply and transforms the voltage of the second power (DC) input from the power supply unit 11 via the power supply line 16.

Each of the endoscope driver circuit board 13, the image processor circuit board 14, and the controller circuit board 15 can be driven by electrical power (the secondary power) supplied from the power supply unit 11 via the power supply line 16. Each of the circuit boards starts respective operations when the power control signal, which is input from the power supply control unit 12 via the signal line 18, is switched from the power cutoff control signal to the power supply control signal. Each of the circuit boards starts the shutdown processing when the power control signal is switched from the power supply control signal to the power cutoff control signal. The shutdown processing is processing for stopping the operations and includes processing to initialize internal setting etc. as an example. Note that in the present embodiment, the start timing of the shutdown processing is different for each of the endoscope driver circuit board 13, the image processor circuit board 14, and the controller circuit board 15. However, the timing may be the same timing, or may be the same timing for only two of the circuit boards. The period of time for the shutdown processing is also different for each of the endoscope driver circuit board 13, the image processor circuit board 14, and the controller circuit board 15. However, the period of time may be the same or may be the same for only two of the circuit boards. In addition, in the controller circuit board 15, the start timing of the shutdown processing is different depending on whether the controller circuit board 15 is accessing the SD card 151, or the USB memory 152, (i.e., during memory access) or not when the power control signal input is switched from the power supply control signal to the power cutoff control signal. More specifically, when the controller circuit board 15 is accessing a memory, the shutdown processing is started after processing to stop the memory access (such as file close processing) and when the controller circuit board 15 is not accessing a memory, the shutdown processing is started immediately.

Note that in the endoscope processor 1 with the above-described configuration, the power supply unit 11 is an example of a power supply circuit that supplies electrical power. Each of the endoscope driver circuit board 13, the image processor circuit board 14, and the controller circuit board 15 is an example of electronic components that is electrically coupled to the power supply circuit, that is operable by electrical power supplied from the power supply circuit, that starts the shutdown processing in response to an input of a stop instruction signal, and that operates when an operation instruction signal is input. The power input control signal is an example of the operation instruction signal, and the power cutoff control signal is an example of the stop instruction signal. The power supply control unit 12 is an example of a signal controller circuit that is electrically coupled to electronic components, that receives an input of a power input state signal or a power cutoff state signal as a power state signal indicating the state of the power supply circuit, that outputs the stop instruction signal when the power cutoff state signal is input, that outputs the operation instruction signal when the power input state signal is input, and that outputs the stop instruction signal at least during the shutdown processing in a case in which the power input state signal is input when the shutdown processing of an electronic component has not been finished. The power supply notice signal is an example of the power input state signal, and the power cutoff notice signal is an example of the power cutoff state signal.

Next, an example of operations of the endoscope processor 1 is explained by using a timing chart.

Figure 2:
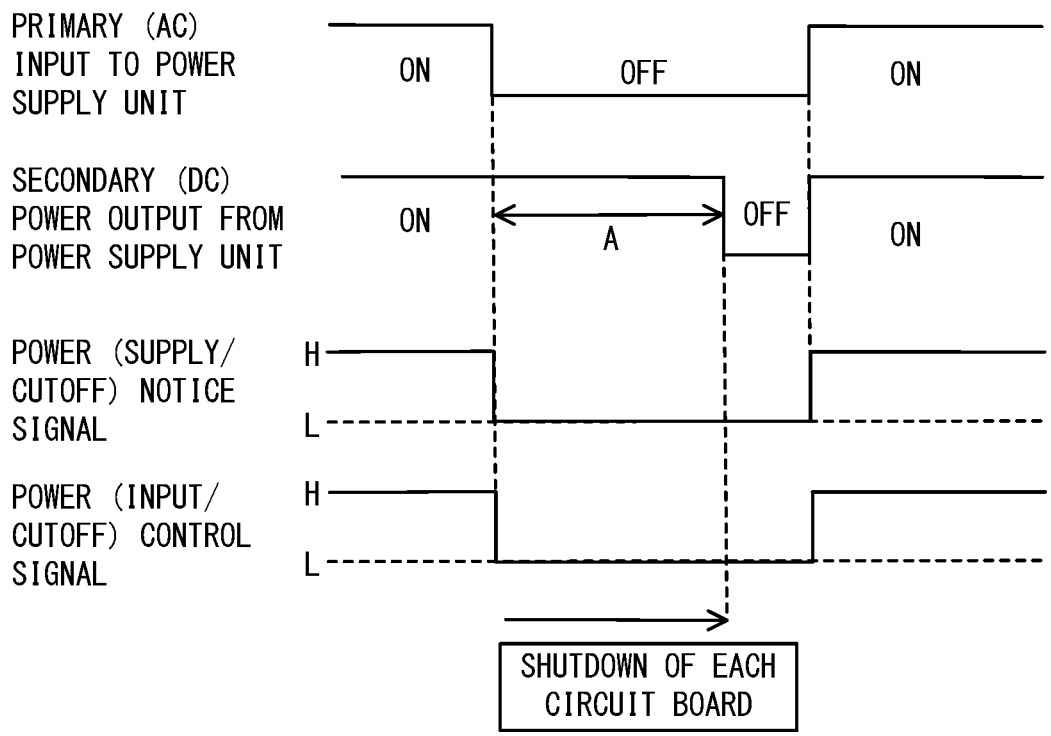
FIG. 2 is a timing chart illustrating an example of operations of the endoscope processor when the primary power input to the power supply unit is cut off and is afterwards restored by normal operation of the power supply switch.
Figure 3:
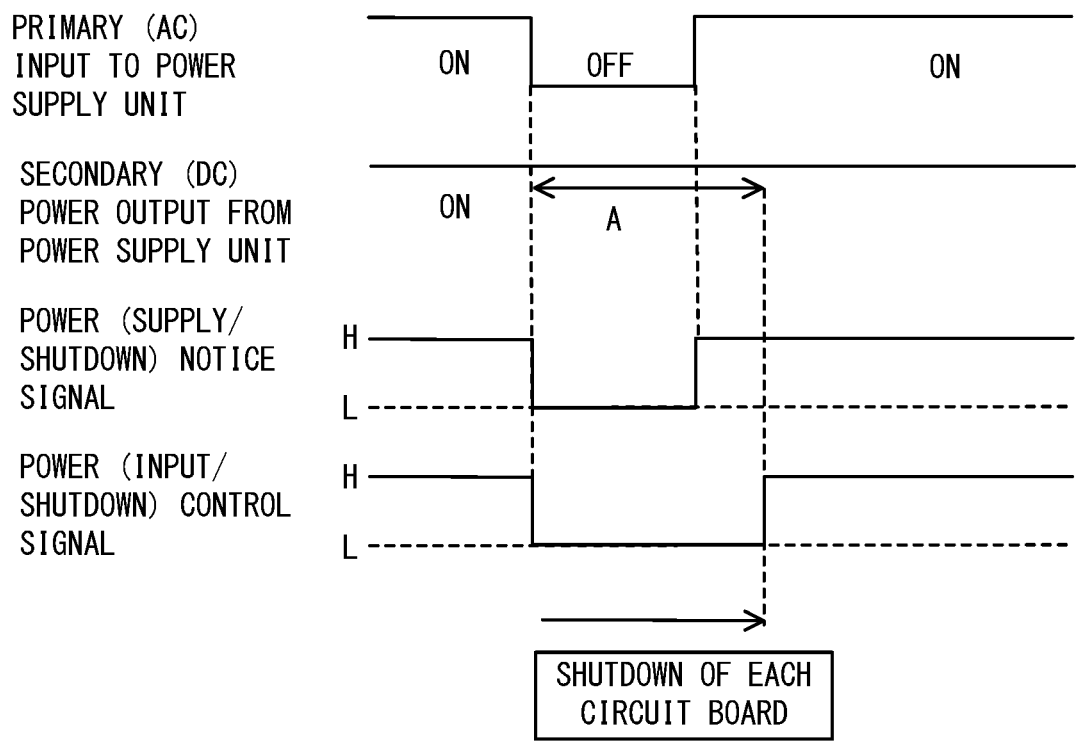
FIG. 3 is a timing chart illustrating an example of operations of the endoscope processor when the primary power input to the power supply unit is cut off and the input is immediately restored by an incorrect operation etc. of the power supply switch.

FIG. 2 is a timing chart illustrating an example of operations of the endoscope processor 1 when the primary power input to the power supply unit 11 is cut off and is afterwards restored by normal operation of the power supply switch. FIG. 3 is a timing chart illustrating an example of operations of the endoscope processor 1 when the primary power input to the power supply unit 11 is cut off and the input is immediately restored by an incorrect operation etc. of the power supply switch.

In FIG. 2 and FIG. 3, timing charts of "PRIMARY (AC) INPUT TO POWER SUPPLY UNIT", "SECONDARY (DC) POWER OUTPUT FROM POWER SUPPLY UNIT", "POWER (SUPPLY/CUTOFF) NOTICE SIGNAL" and "POWER (INPUT/CUTOFF) CONTROL SIGNAL" are provided in this order from the top. "PRIMARY (AC) INPUT TO POWER SUPPLY UNIT" indicates the input or the cutoff of the primary power in the power supply unit 11. "ON" indicates the primary power being input and "OFF" indicates the primary power being cut off. "SECONDARY (DC) POWER OUTPUT FROM POWER SUPPLY UNIT" indicates presence/absence of the secondary power output from the power supply unit 11. "ON" indicates the secondary power output being present and "OFF" indicates the secondary power output being absent. "POWER (SUPPLY/ CUTOFF) NOTICE SIGNAL" indicates a power notice signal output from the power supply unit 11. An H (High) level of the power notice signal indicates a power supply notice signal and an L (Low) level of the power notice signal indicates a power cutoff notice signal. "POWER (INPUT/ CUTOFF) CONTROL SIGNAL" indicates a power control signal output from the power supply control unit 12. An H level of the power control signal indicates a power input control signal and an L level of the power control signal indicates a power cutoff control signal.

As illustrated in FIG. 2, in an example of operations in a case in which the power supply switch is normally operated, when the primary power input to the power supply unit 11 is turned from ON to OFF, the secondary power being turned ON is maintained for the prescribed period of time A by the charge in the capacitor included in the AC-DC converter circuit 111 in the power supply unit 11. In addition, in the power supply unit 11, the output power notice signal is switched from the H level to the L level in response to the primary power being turned OFF.

In response, in the power supply control unit 12, the power control signal output is switched from the H level to the L level, and since then, the output of the power control signal is maintained at the L level for the prescribed period of time A.

When the power control signal input is switched from the H level to the L level, each of the endoscope driver circuit board 13, the image processor circuit board 14, and the controller circuit board 15 start the shutdown processing at the corresponding timing. For example, in the controller circuit board 15, the shutdown processing is started after the processing to stop the memory access. During the prescribed period of time A, the shutdown processing will be all finished in each of the endoscope driver circuit board 13, the image processor circuit board 14, and the controller circuit board 15, and each of the circuit boards becomes a state of ready for cutoff of the secondary power.

When the prescribed period of time A has elapsed, the secondary power is turned OFF in the power supply unit 11.

Later, when the primary power that was turned OFF is turned ON again in the power supply unit 11, the state of the secondary power being ON is resumed and the power notice signal output is switched from the L level to the H level. In response, the power control signal output is switched from the L level to the H level in the power supply control unit 12.

When the power control signal input is switched from the L level to the H level, each of the endoscope driver circuit board 13, the image processor circuit board 14, and the controller circuit board 15 starts respective operations.

As illustrated in FIG. 3, in an example of operations in a case of an incorrect operation of the power supply switch, when the primary power is turned from ON to OFF in the power supply unit 11 and the primary power is turned ON again before the elapse of the prescribed period of time A, the secondary power being ON is maintained in the power supply unit 11 for a period of time from the primary power being turned OFF to the primary power being turned ON again, by the charge in the capacitor in the AC-DC converter circuit 111. In the power supply unit 11, in response to the primary power being turned OFF, the power notice signal output is switched from the H level to the L level, and later, in response to the primary being turned ON again, the power notice signal output is switched from the L level to the H level.

In the power supply control unit 12, the power notice signal input is switched from the H level to the L level, the power control signal output is switched from the H level to the L level, and since then, the output of the power control signal is maintained at the L level for the prescribed period of time A. Note that in this example of operations, the power notice signal is switched from the L level to the H level before the elapse of the prescribed period of time A from a point in time at which the power notice signal was switched from the H level to the L level. However, during the prescribed period of time A, even when the power notice signal is switched to the H level, the output of the power control signal is maintained at the L level. When the prescribed period of time A has elapsed, in the power supply control unit 12, because the power notice signal at that time is at the H level, the power control signal is switched from the L level to the H level.

When the power control signal input is switched from the H level to the L level, each of the endoscope driver circuit board 13, the image processor circuit board 14, and the controller circuit board 15 starts the shutdown processing at the corresponding timing. During the prescribed period of time A, the shutdown processing will be all finished in each of the endoscope driver circuit board 13, the image processor circuit board 14, and the controller circuit board 15, and each of the circuit boards becomes a state of ready for cutoff of the secondary power. After the prescribed period of time A has elapsed, each of the circuit boards starts respective operations when the power control signal input is switched from the L level to the H level.

According to the present embodiment, when the primary power input to the power supply unit 11 is cut off and the input is resumed immediately after the shutdown by incorrect operations of the power supply switch etc., the output of the power cutoff control signal is maintained as the output of the power supply control unit 12 until the elapse of the prescribed period of time A from a point in time of the cutoff of the primary power. The shutdown processing is performed without fail in each of the endoscope driver circuit board 13, the image processor circuit board 14, and the controller circuit board 15, and each of the circuit boards restarts in an initialized state. As a result, differences in startup states will not be made between the endoscope driver circuit board 13, the image processor circuit board 14, and the controller circuit board 15 after the restart. Because the differences will not be made, the risk of the endoscope processor 1 not operating normally is eliminated.

Note that the following modification may be made to the present embodiment.

For example, the power supply control unit 12 may be configured to output a power cutoff signal, to make an inquiry to each of the endoscope driver circuit board 13, the image processor circuit board 14, and the controller circuit board 15 to inquire whether the shutdown processing is finished or not, and to maintain the output of the power cutoff control signal until a response of the shutdown processing being finished is received from each of the circuit boards.

Another example is that the power supply control unit 12 may be configured to output a power cutoff control signal and to maintain the output of the power cutoff control signal until a notice of the shutdown processing being finished is received from each of the endoscope driver circuit board 13, the image processor circuit board 14, and the controller circuit board 15.

The present embodiment provides three examples of the electronic components: the endoscope driver circuit board 13; the image processor circuit board 14; and the controller circuit board 15. However, the number of examples is not limited to three, and the number may be one or more than one but other than three.

Second Embodiment

FIG. 4 is a diagram illustrating an example of configuration of an endoscope processor that is the power supply control system according to the second embodiment.

As illustrated in FIG. 4, an endoscope processor 2 according to the second embodiment includes a power supply module 21 and three modules 22 (also referred as the module A, the module B, and the module C). The power supply module 21 and the three modules 22 are electrically coupled to each other via a power supply line 23 that is a power supply pathway. The power supply module 21 and each of the modules 22 are electrically coupled to each other via a signal line 24 (24a, 23b, or 24c) that is a regulatory pathway. The module A and the module B are electrically coupled to each other via a transmission line 25 provided between I/Fs of the modules. The module B and the module C are electrically coupled to each other via a transmission line 26 provided between I/Fs of the modules.

The power supply module 21 includes a unit power supply 211 and a module power supply control unit 212. The unit power supply 211 supplies power to each of the modules 22 via the power supply line 23. The module power supply control unit 212 controls the startup and cutoff of a local power supply 221 of each of the modules 22.

Each of the modules 22 is a circuit board (circuit) to carry out prescribed processing and includes the local power supply 221 and a multiple-power-supply-operation device 222. Note that the local power supply 221 and the multiple-power-supply-operation device 222 included in the module A are also referred to as the local power supply A and the multiple-power-supply-operation device A. The local power supply 221 and the multiple-power-supply-operation device 222 included in the module B are also referred to as the local power supply B and the multiple-power-supply-operation device B. The local power supply 221 and the multiple-power-supply-operation device 222 included in the module C are also referred to as the local power supply C and the multiple-power-supply-operation device C.

In each of the modules 22, the local power supply 221 is a power supply IC (Integrated Circuit) to start up the multiple-power-supply-operation device 222, supplies multiple power supplies to the multiple-power-supply-operation device, and controls the startup and cutoff of each of the multiple power supplies.

The multiple-power-supply-operation device 222 is a device (e.g., CPU (Central Processing Unit) or FPGA (FIELD-Programmable Gate Array), which are operated by the multiple power supplies (e.g., a core power supply, an IO (Input/Output) power supply). The multiple-power-supply-operation device 222 is provided with an I/F for signal transmission with other multiple-power-supply-operation device 222, and control of the I/F is carried out by receiving power from the local power supply 221. More specifically, the multiple-power-supply-operation device A is provided with an I/F for signal transmission with the multiple-power-supply-operation device B via the transmission path 25, and control of the I/F is carried out by receiving power from the local power supply A. The multiple-power-supply-operation device B is provided with an I/F for signal transmission with the multiple-power-supply-operation device A via the transmission path 25 and an I/F for signal transmission with the multiple-power-supply-operation device C via the transmission path 26, and control of these two I/Fs is carried out by receiving power from the local power supply B. The multiple-power-supply-operation device C is provided with an I/F for signal transmission with the multiple-power-supply-operation device B via the transmission path 26, and control of the I/F is carried out by receiving power from the local power supply C.

FIG. 5 is a timing chart illustrating an example of a startup sequence of the multiple-power-supply-operation device A under the control of the local power supply A in module A. Here, the multiple-power-supply-operation device A is a device operated by three power supplies including A-1 power, A-2 power, and A-3 power, and the A-2 power is control power for the I/F to perform signal transmission with the multiple-power-supply-operation device B. In FIG. 5, "A-1 POWER CONTROL", "A-2 POWER CONTROL", and "A-3 POWER CONTROL" are control signals of the respective power supplies.

As illustrated in FIG. 5, in the startup sequence of the multiple-power-supply-operation device A, "A-1 POWER CONTROL", "A-2 POWER CONTROL", and "A-3 POWER CONTROL" are control signals that are switched from OFF to ON at the same timing within a certain period of time. In other words, the power supplies are controlled to start up at the same time.

Figure 6:
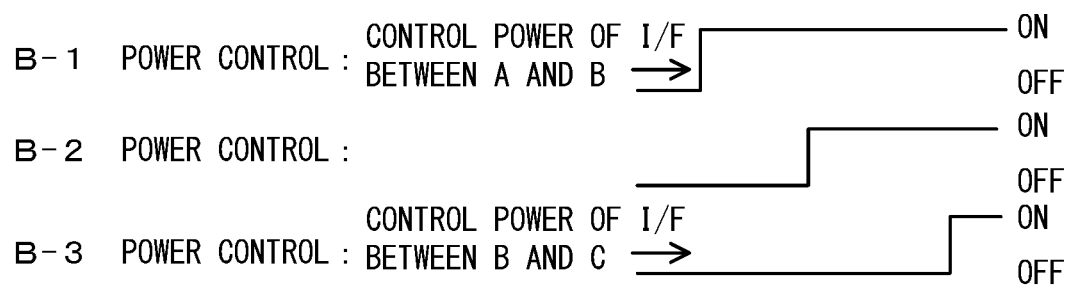
FIG. 6 is a timing chart illustrating an example of a startup sequence of the multiple-power-supply-operation device B under the control of the local power supply B in module B.

FIG. 6 is a timing chart illustrating an example of a startup sequence of the multiple-power-supply-operation device B under the control of the local power supply B in module B. Here, the multiple-power-supply-operation device B is a device operated by three power supplies including B-1 power, B-2 power, and B-3 power. The B-1 power is control power for the I/F to perform signal transmission with the multiple-power-supply-operation device A, and the B-3 power is control power for the I/F to perform signal transmission with the multiple-power-supply-operation device C. In FIG. 6, "B-1 POWER CONTROL", "B-2 POWER CONTROL", AND "B-3 POWER CONTROL" are control signals of the respective power supplies.

As illustrated in FIG. 6, in the startup sequence of the multiple-power-supply-operation device B, "B-1 POWER CONTROL", "B-2 POWER CONTROL", and "B-3 POWER CONTROL" are control signals that are switched from OFF to ON in sequence. In other words, the power supplies are controlled to start up in sequence.

Figure 7:
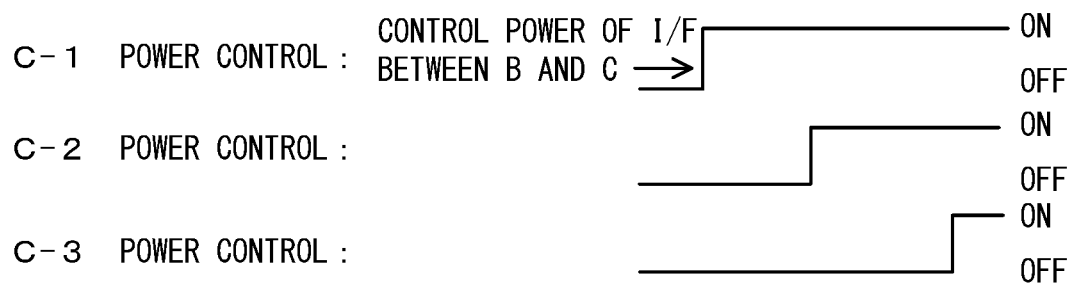
FIG. 7 is a timing chart illustrating an example of a startup sequence of the multiple-power-supply-operation device C under the control of the local power supply C in module C.

FIG. 7 is a timing chart illustrating an example of a startup sequence of the multiple-power-supply-operation device C under the control of the local power supply C in module C. Here, the multiple-power-supply-operation device C is a device operated by three power supplies including C-1 power, C-2 power, and C-3 power, and the C-1 power is control power for the I/F to perform signal transmission with the multiple-power-supply-operation device B. In FIG. 7, "C-1 POWER CONTROL", "C-2 POWER CONTROL", and "C-3 POWER CONTROL" are control signals of the respective power supplies.

As illustrated in FIG. 7, in the startup sequence of the multiple-power-supply-operation device C, similarly to the startup sequence of the multiple-power-supply-operation device B, "C-1 POWER CONTROL", "C-2 POWER CONTROL", and "C-3 POWER CONTROL" are control signals that are switched from OFF to ON in sequence. In other words, the power supplies are controlled to start up in sequence.

When the multiple-power-supply-operation device 222 in each of the modules 22 has such a startup sequence as provided in FIG. 5 to FIG. 7, the module power supply control unit 122 in the power supply module 21 controls the local power supply 221 in each of the modules 22 in the following manner.

Figure 8:
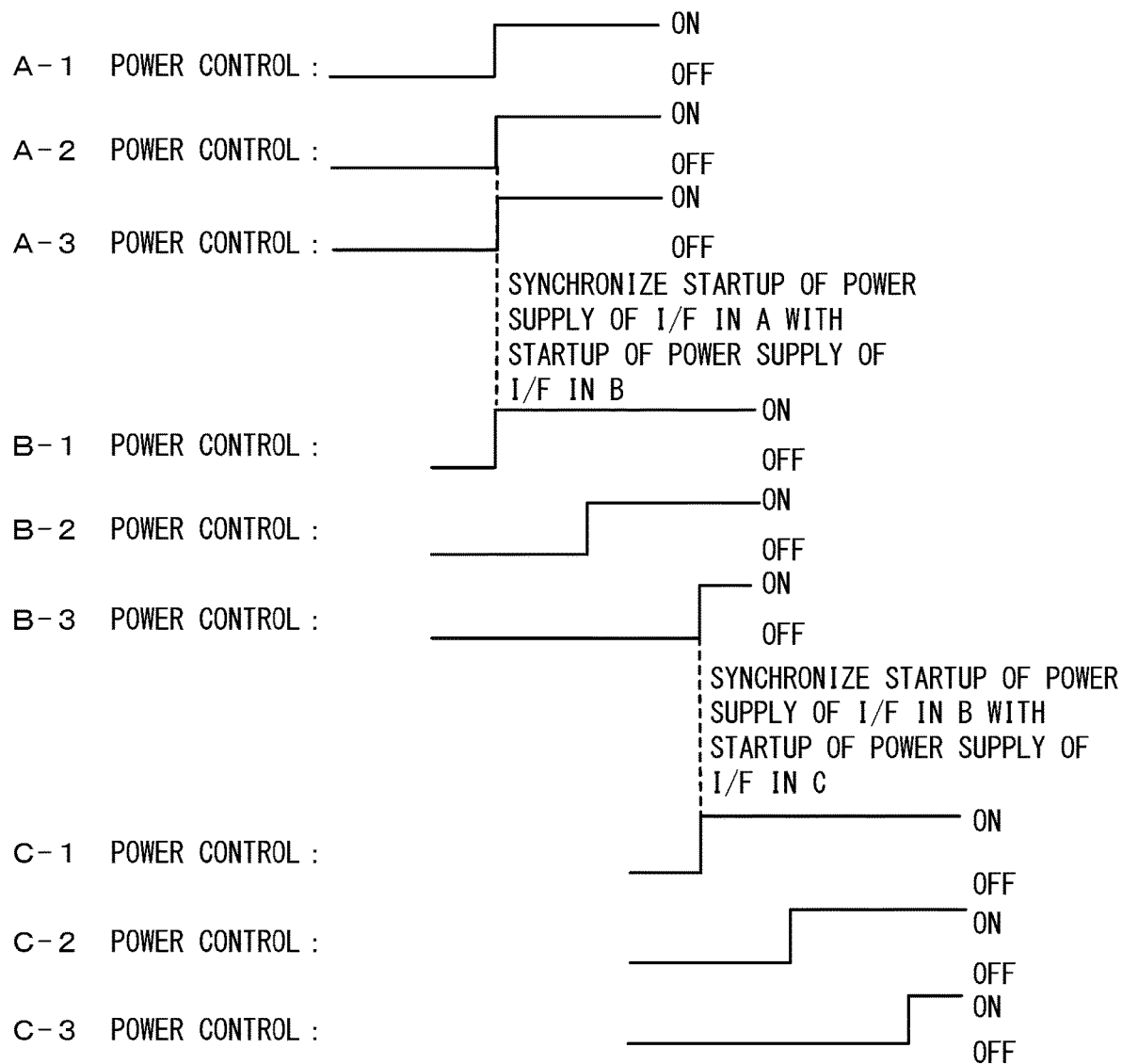
FIG. 8 is a diagram for explaining an example of control by the module power supply control unit.

FIG. 8 is a diagram for explaining an example of control by the module power supply control unit 212.

As illustrated in FIG. 8, the module power supply control unit 212 controls the startup of the local power supply 221 of each of the modules 22 so that the B-1 power in the multiple-power-supply-operation device B starts up in synchronization with the startup (rise) of the A-2 power of the multiple-power-supply-operation device A and the C-1 power in the multiple-power-supply-operation device C starts up in synchronization with the startup (rise) of the B-3 power of the multiple-power-supply-operation device B.

With this control, the A-2 power, which is control power of the I/F connected to one end of the transmission path 25, and the B-1 power, which is control power of the I/F connected to another end of the transmission path 25, can be started at the same time. In addition, the B-3 power, which is control power of the I/F connected to one end of the transmission path 26, and the C-1 power, which is control power of the I/F connected to another end of the transmission path 26, can be started at the same time.

This control can prevent latch-up, which is caused by power transmission from an I/F at one end to an I/F at another end via a transmission path. The latch-up can occur between the A-2 power and the B-1 power and between the B-3 power and the C-1 power when a power supply at one end has already started up but a power supply at another end has not yet started.

Note that in the example explained with reference to FIG. 5 to FIG. 8, an example of control in a case of startup of the local power supply 221 in each of the modules 22 (multiple power supplies in the multiple-power-supply-operation device 222 in each of the modules 22) is provided. A control in a case of cutoff of the local power supply 221 in each of the modules 22 (multiple power supplies in the multiple-power-supply-operation device 222 in each of the modules 22) is carried out in the same manner. In this case, the control power of the two I/Fs connected via a transmission path may be controlled so that the control power of an I/F at one end is cut off in synchronization with the cutoff of the control power of an I/F at another end.

As described above, according to the present embodiment, the module power supply control unit 212 controls the startup and cutoff of the local power supply 221 in each of the modules 22 so as to synchronize with the timing of the startup and cutoff of the control power for I/Fs to perform signal transmission in the multiple-power-supply-operation device 222 in each of the modules 22. As a result, occurrence of latch-up due to unintended power transmission can be prevented. In addition, failure of the multiple-power-supply-operation device 222 caused by the occurrence of latch-up can be prevented.

Accordingly, in the present embodiment, an I/F that is provided for signal transmission does not need a buffer or a switch etc., for preventing the power transmission to the I/F. When buffers or switches etc. are used, the transmission paths that can be used are limited to those of a transmission rate that the performance of the buffers or switches etc., can accommodate to. However, the implementation of the present embodiment is not limited by the transmission rate of transmission paths.

Third Embodiment

An endoscope processor that is the power supply control system according to the third embodiment is provided with a module (e.g., circuit boards (circuit)) etc.

Figure 9:
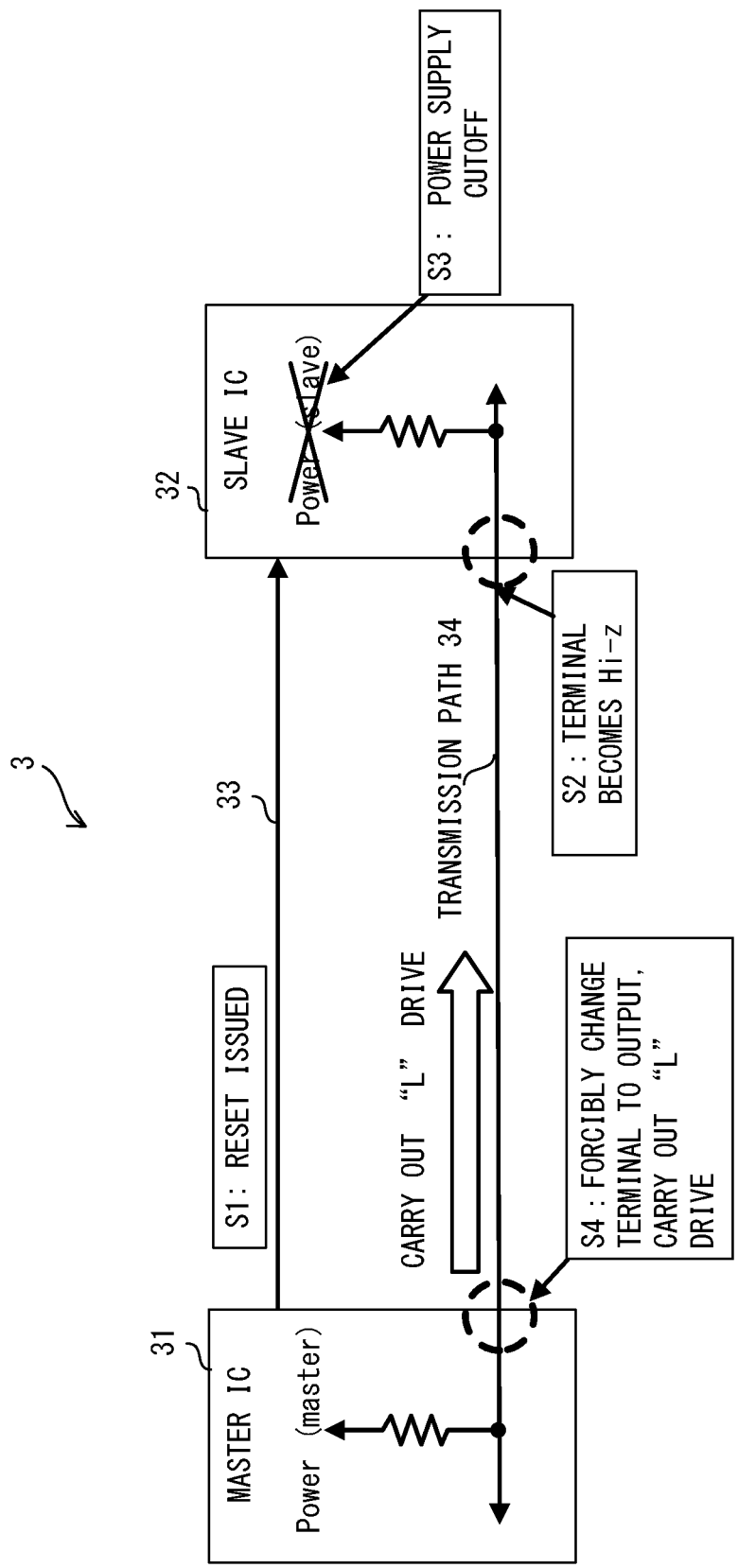
FIG. 9 is a diagram illustrating an example of configuration of a module included in an endoscope processor that is a power supply control system according to the third embodiment.

FIG. 9 is a diagram illustrating an example of configuration of the module.

As illustrated in FIG. 9, a module 3 provided in the endoscope processor according to the present embodiment includes a master IC 31 and a slave IC 32 that are electrically connected via a signal line 33 and a transmission path 34.

The master IC 31 outputs a reset signal to the slave IC 32 via the signal line 33. The master IC 31 is provided with a terminal (I/F) and a power supply (Power (master)) etc. for signal transmission with the slave IC 32 via the transmission path 34.

The slave IC 32 receives an input of a reset signal from the master IC 31 via the signal line 33. The slave IC 32 is provided with a terminal (I/F) and a power supply (Power (slave)) etc. for signal transmission with the master IC 31 via the transmission path 34.

In the module 3 with the above-described configuration, when a reset signal is output from the master IC 31 to the slave IC 32, the slave IC 32 restarts (restores) the power supply (Power (slave)).

More specifically, when a reset signal is output (reset issued) from the master IC 31 to the slave IC 32 (S1), the slave IC 32 stops the input/output of signals for the terminals being at Hi-Z (high impedance) (S2), and the power supply (Power (slave)) is cut off (S3). In the master IC 31, the setting of the terminal are forcibly changed into an output mode and "L" drive ("L" output) from the terminal is carried out (S4).

Figure 10:
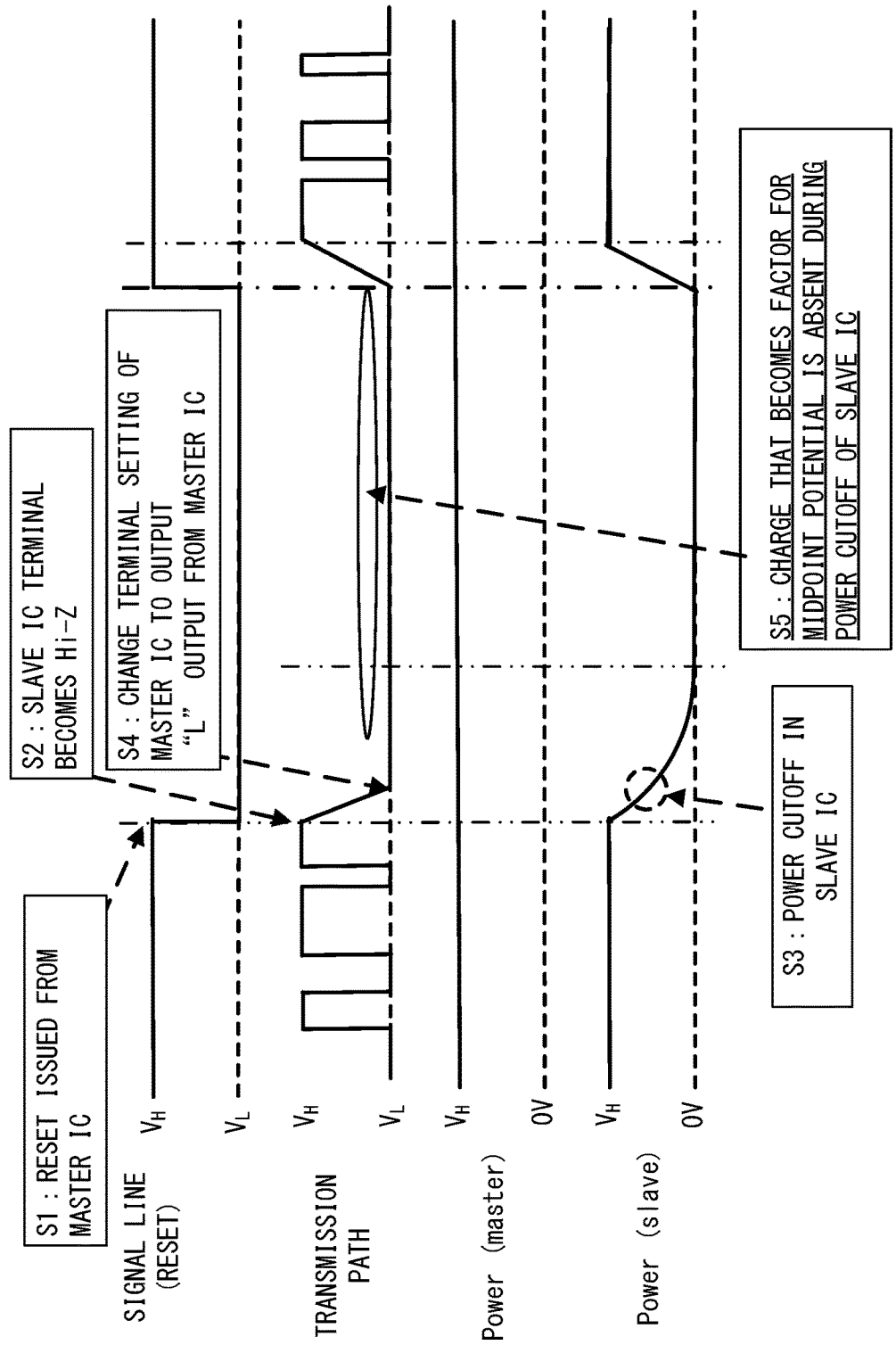
FIG. 10 is a diagram illustrating an example of changes in electrical potential in a signal line, a transmission path, a power supply (Power (master)) of a master IC, and a power supply (Power (slave)) of a slave IC.

FIG. 10 is a diagram illustrating an example of changes in electrical potential at that time in the signal line 33, the transmission path 34, the power supply (Power (master)) of the master IC 31, and the power supply (Power (slave)) of the slave IC 32.

As illustrated in FIG. 10, when a reset signal is output (reset issued) from the master IC 31 (S1), the potential switches from $V_H$ to $V_L$ in the signal line 33. In response, the terminal of the slave IC 32 becomes Hi-Z (S2), and the potential starts to drop in the transmission path 34. The power supply (Power (slave)) of the slave IC 32 is cut off (S3). The potential starts to drop from $V_H$ and reaches 0. Then, the setting of the terminal of the master IC 31 is changed to an output mode and "L" output from the terminal is carried out (S4). The potential becomes $V_L$ in the transmission path 34. Afterwards, while the power supply (Power (slave)) of the slave IC 32 is cut off, the potential of the transmission path 34 remains $V_L$, and charge that becomes a factor for the midpoint potential is absent from the transmission path 34 (S5). Note that the potential of the power supply (Power (master)) of the master IC 31 remains at $V_H$.

In this manner, according to the present embodiment, when the slave IC 32 restarts the power supply in response to a reset signal from the master IC 31, power transmission from the master IC 31 to the slave IC 32 via the transmission path 34 does not occur while the power supply (Power (slave)) of the slave IC 32 is cut off. Accordingly, occurrence of latch-up can be prevented, and failure of the slave IC 32 caused by the occurrence of latch-up can be prevented.

As a result, similarly to the second embodiment, a terminal (I/F) does not need a buffer or a switch etc., to prevent the power transmission, and the implementation of the present embodiment is not limited by the transmission rate of the transmission path.

The above-described embodiments are specific examples of the present invention provided to facilitate the understanding of the invention. The present invention is not limited to the above-described embodiments. Various modifications and changes can be made to the present invention without departing from the concept of the present invention defined in the scope of the claims.

What is claimed is:

1. A power supply control system comprising:
   a power supply circuit configured to supply power;
   a plurality of electronic components configured to be electrically coupled to the power supply circuit, the plurality of electronic components being configured to be operable by the power supplied from the power supply circuit, the plurality of electronic components being configured to start shutdown processing in response to an input of a stop instruction signal, and the plurality of electronic components being configured to operate when an operation instruction signal is input; and a signal control circuit configured to be electrically coupled to the plurality of electronic components, the signal control circuit being configured to receive a power input state signal or a power cutoff state signal as a power state signal indicating a state of the power supply circuit, the signal control circuit being configured to output the stop instruction signal when the power cutoff state signal is input, the signal control circuit being configured to output the operation instruction signal when the power input state signal is input, and the signal control circuit being configured to continuously output the stop instruction signal at least during the shutdown processing when the power input state signal is input when the shutdown processing of at least one electronic component of the plurality of electronic components is not completed and maintains the output of the stop instruction signal until the shutdown processing of the at least one electronic component of the plurality of electronic components is completed.

2. The power supply control system according to claim 1, wherein the signal control circuit outputs the operation instruction signal after the shutdown processing is completed.

3. The power supply control system according to claim 1, wherein the power supply circuit supplies power to the plurality of the electronic components.

4. The power supply control system according to claim 1, wherein the signal control circuit outputs the operation instruction signal after the shutdown processing of the plurality of the electronic components is all completed.

5. The power supply control system according to claim 3, wherein the plurality of the electronic components are different from each other in shutdown processing time.

6. A power supply control method comprising:

receiving an input of a power input state signal or a power cutoff state signal as a power state signal indicating a state of a power supply circuit that supplies power to a plurality of electronic components;

outputting a stop instruction signal to at least one electronic component of the plurality of electronic components when the power cutoff state signal is input and causing the at least one electronic component of the plurality of electronic components to start shutdown processing; and outputting the stop instruction signal to the at least one electronic component of the plurality of electronic components at least during the shutdown processing when the power input state signal in input when the shutdown processing of the at least one electronic component of the plurality of electronic components is not completed and maintains the output of the stop instruction signal until the shutdown processing of the at least one electronic component of the plurality of electronic components is completed.

* * * * *